United States Patent [19]

Klemm

[11] Patent Number: Plant 7,015

[45] Date of Patent: Sep. 5, 1989

[54] GERANIUM NAMED KLERISSA

[76] Inventor: Siegfried Klemm, Hanfacker 8, D-7000 Stuttgart 50, Fed. Rep. of Germany

[21] Appl. No.: 244,308

[22] Filed: Sep. 15, 1988

[51] Int. Cl.[4] ..... A01H 5/00
[52] U.S. Cl. ..... Plt./68
[58] Field of Search ..... Plt./68

*Primary Examiner*—Robert E. Bagwill
*Attorney, Agent, or Firm*—Chas. W. Rummler

[57] ABSTRACT

A new and distinct geranium cultivar particularly distinguished by the intensive red coloration of its well filled blooming clusters which stand well above a compact mass of dark green foliage, thereby providing a sharp and very attractive appearance for the blooming plant. The plant itself is very bushy and is of a relatively low overall height of about 30 cm. above the soil, the growth rate being medium but upright and compact with good strength. The floral persistence is very good and the lasting quality of the blooming plant is very long from early Spring to late Fall.

1 Drawing Sheet

BACKGROUND OF THE NEW PLANT

My new geranium cultivar originated as a seedling of unknown parentage found in my nursery at Stuttgart, West Germany, among a stand of geranium varieties maintained by me for breeding purposes. This new plant was discovered in 1984 and because of its presentation of the flower clusters, well above a body of dark green leaves, this plant was selected for propagation, which was done by me and under by direction with cuttings at Stuttgart and carried on through several successive generations whereby to determine the homogeneity could be assured. Thus it was determined conclusively that the distinctive and novel characteristics of this new plant would hold true from generation to generation and appeared to be firmly fixed. The new plant is weather-proof, resistant against Botrytis, and has a substantial decoration and market value.

DESCRIPTION OF THE DRAWING

My new geranium cultivar is illustrated by the accompanying full color photographic drawing, which illustrates a potted plant showing the general character of the new variety with respect to both the foliage and flower clusters, the colors shown being as true to that specified herein as is reasonably possible to obtain by conventional, professional photographic procedures.

DESCRIPTION OF THE NEW PLANT

The following is a detailed description of my new geranium cultivar based upon observations made in the Spring of 1988 of plants of this variety grown in greenhouse, as well as outdoors, the color designation being according to The R.H.S. Colour Chart of The Royal Horticultural Society of London, England.

THE PLANT

Origin: Seedling.
Parentage: Unknown.
Classification:
- *Botanic.*—*Pelargonium zonal* hybrid.
- *Commercial.*—Geranium.

Form: Very bushy and of a height of about 30 cm. above the soil.

Growth: Vigorous, upright and compact with very good strength.
Growth rate: Medium.
Branching character: Very good.
Flower stem length: About 15 cm.
Foliage:
- *Quantity.*—Moderately abundant.
- *Size of leaf.*—About 8 cm. long and 6 cm. wide.
- *Leaf shape.*—Reniform and cup-like.
- *Margin type.*—Bicrenate.
- *Ribs and veins.*—Five main veins on each leaf. Color: Upper side — Very Dark Green but lighter in the midportion. Under side — Green with Light Green veins.

THE BUD

Size: Normal.
- *Diameter.*—About 10 mm.
- *Length.*—About 12 to 13 mm.

Shape: Ovoid to globular with pointed apex.
Rate of opening: Medium.
Color of florets:
- *When sepals first divide.*—Red.
- *When petals begin to unfurl.*—Red.

Sepals:
- *Number.*—Five.
- *Shape.*—Linear.
- *Character.*—The sepals stand up when the flowers open.
- *Color.*—Inside — Green. Outside — Dark Green.

Flower stem:
- *Length.*—About 10 to 15 cm.
- *Character.*—Upright and rigid.
- *Color.*—Dark Green.

THE INFLORESCENCE

Blooming habit: Continuous and profusely from early Spring to late Fall.
Cluster:
- *Size.*—Medium. Diameter — About 11 cm.
- *Number of florets.*—About 60 to 70 per cluster.

Florets:
- *Size.*—Medium. Diameter — About 3.8 to 4 cm.
- *Borne.*—Singly on the umbel stem of a cluster.
- *Shape.*—When bloom first opens, cup-shaped. When bloom matures, flat.

Petalage:
*Number of petals.*—Up to ten.
*Arrangement.*—Imbricated.
*Form.*—Broad ovate with entire margin and round apex.
*Texture.*—Soft.
*Appearance.*—Velvety.
*Color.*—RHS 44-B.

Petaloids:
*Number.*—Three to four.
*Size.*—About 5 to 6 mm.
*Color.*—Intensive Red.

Flower stem:
*Length.*—About 14 to 15 cm.
*Color.*—Dark Green.
*Character.*—Upright and very strong.

Effect of weather: None.
Discoloration after full bloom: None.
Frangrance: None.
Persistence: Very good.
Lasting quality: Very good. The petals stay on the florets for about sixteen days.
Disease resistance: The plant is resistant to Botrytis as observed in the region of Stuttgart, West Germany, in 1987.

THE REPRODUCTIVE ORGANS

Stamens:
*Number.*—Seven.

*Arrangement.*—In a ring around the ovaries.
*Anthers.*—Size: About 1.5 mm. Color: Dark Orange.
*Filaments.*—Length: About 4 to 5 mm. Color: White.
*Pollen.*—Color: Orange.

Pistil:
*Number.*—One.
*Style.*—Length: About 3 to 4 mm. Color: Light Green.
*Stigma.*—Five cells. Color: Light Red.

THE FRUIT

Fertility: The fruit is fertile.
Shape: Ovoid.
Color at maturity: Dark Brown.

This new geranium variety has a beautiful, very intensive, double-flowering red color. The plant growth is very bushy and the very dark green leaves give a nice contrast to the red flower clusters. The clusters last very long on the plant, there are many of them, and the plant has good resistance against Botrytis in wet seasons.

I claim:

1. The new geranium cultivar, as herein shown and described, particularly distinguished by its bright red flower clusters standing well above a bushy, compact foliage body with dark green leaves.

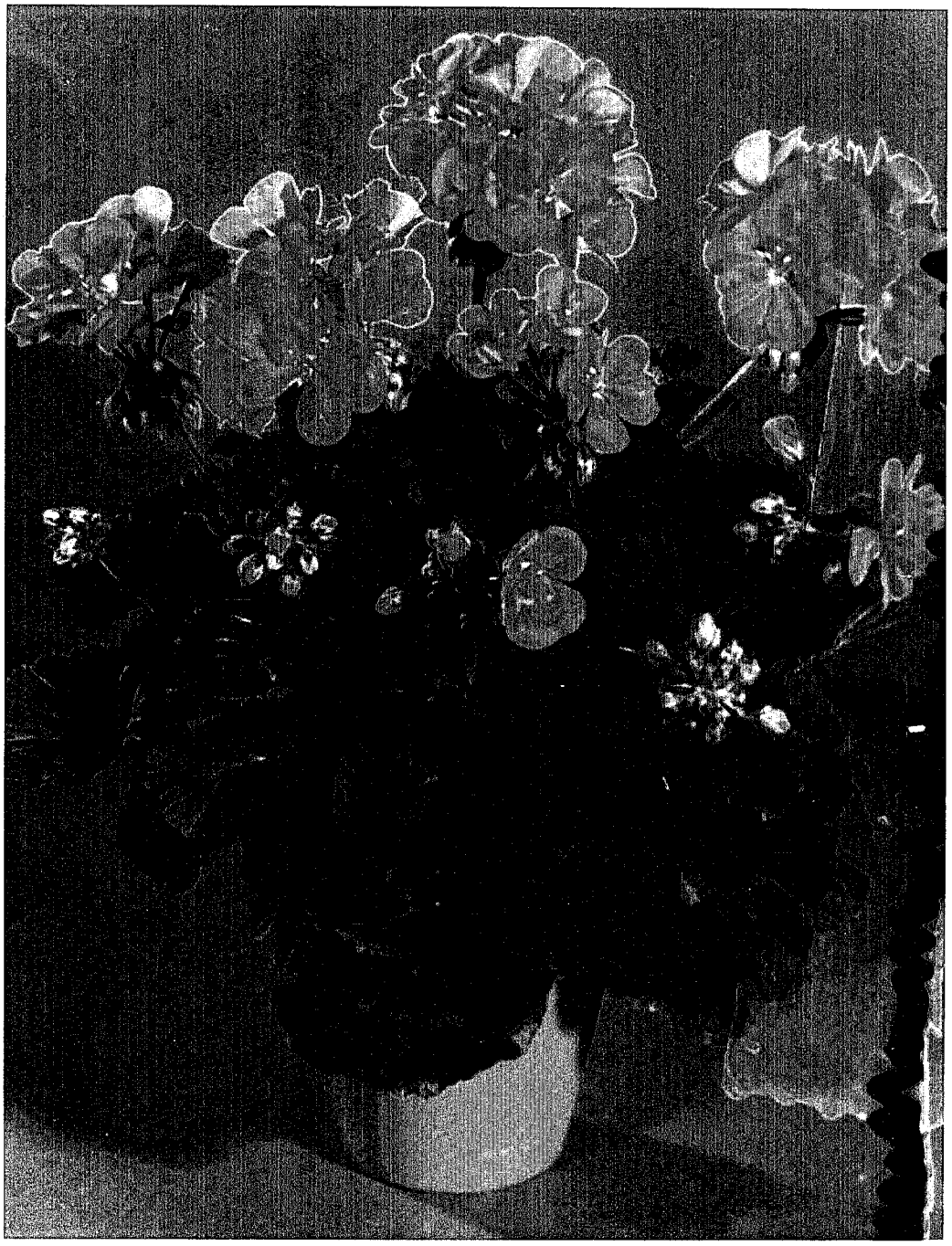

* * * * *